(12) United States Patent
Perner

(10) Patent No.: US 7,711,495 B2
(45) Date of Patent: May 4, 2010

(54) METHODS FOR AUTOMATICALLY IDENTIFYING MICROORGANISMS COLLECTED ON A CARRIER

(76) Inventor: Petra Perner, Kurt-Eisner-Str. 81, Leipzig (DE) 04275

(*) Notice: Subject to any disclaimer, the term of this patent is extended or adjusted under 35 U.S.C. 154(b) by 683 days.

(21) Appl. No.: 10/574,176

(22) PCT Filed: Oct. 1, 2004

(86) PCT No.: PCT/DE2004/002229

§ 371 (c)(1),
(2), (4) Date: Nov. 17, 2006

(87) PCT Pub. No.: WO2005/031319

PCT Pub. Date: Apr. 7, 2005

(65) Prior Publication Data

US 2007/0207451 A1    Sep. 6, 2007

(30) Foreign Application Priority Data

Oct. 2, 2003   (DE) ................................ 103 47 123

(51) Int. Cl.
*G01N 33/48* (2006.01)
(52) U.S. Cl. .................. 702/21; 702/127; 702/167; 702/193; 703/11; 382/128; 382/133; 382/165; 382/181; 382/285
(58) Field of Classification Search .............. None
See application file for complete search history.

(56) References Cited

U.S. PATENT DOCUMENTS

| | | | |
|---|---|---|---|
| 4,160,601 A | 7/1979 | Jacobs | 356/404 |
| 5,162,990 A | 11/1992 | Odeyale et al. | 364/413.1 |
| 5,663,057 A | 9/1997 | Drocourt et al. | 435/40.5 |
| 5,891,394 A | 4/1999 | Drocourt et al. | 422/50 |
| 2003/0096302 A1* | 5/2003 | Yguerabide et al. | 435/7.1 |

FOREIGN PATENT DOCUMENTS

GB    2 254 414    10/1992

OTHER PUBLICATIONS

Dugan et al., "Quantitative Infrared Photoanalysis of Selected Bacteria", 1974, Applied Microbiology, vol. 28, No. 2, pp. 205-211.*

* cited by examiner

*Primary Examiner*—Carolyn L. Smith
(74) *Attorney, Agent, or Firm*—Gudrun E. Huckett

(57) ABSTRACT

For automatic identification of microorganisms collected on a carrier, a color image of the carrier surface with collected microorganisms is recorded and digitalized. The digitalized image is converted into a grayscale image and optionally converted subsequently into a silhouette image. When microorganisms are present, an image is produced with full-surface labeled objects of a first grayscale and a background of a second grayscale. Objects are identified in the grayscale and/or silhouette image by a model-based comparative method. Contours of the objects are marked in the color or grayscale image. Features of the objects in the color image and/or grayscale image are determined. The objects are classified based on the features. The classified objects are indicated and/or saved as species, name and/or code. Non-classified objects are indicated and/or saved as color, grayscale and/or silhouette image. Non-classified objects are subsequently discarded or added as a new case to the classification system.

8 Claims, No Drawings

METHODS FOR AUTOMATICALLY IDENTIFYING MICROORGANISMS COLLECTED ON A CARRIER

BACKGROUND OF THE INVENTION

The invention concerns methods for automatically identifying microorganisms collected on a carrier that are particles, airborne or present in water, in the form of fungal spores and bacteria.

As is known in the art, the identification of airborne particles or particles present in water is done by collecting these particles on a carrier. This carrier is advantageously positioned in a channel or at the end of a channel for supply air or water. In this connection, the carrier is a filter or a body with a coating of an adhesive. After collection, the particles are incubated on culture media in microbiological laboratories. After several days, an analysis of the colonies obtained in this way can be done. The colonies that all can be traced back to only a single collected germ are coarsely preexamined manually in regard to color, shape, and structure. A more precise determination of the species of germ is possible only after their individualization as well as growth tests and metabolic tests. This usually takes several weeks. Also, the identification of these colonies is done manually.

The invention has the object to automatically identify microorganisms collected on a carrier that are particles, airborne or present in water, in the form of fungal spores and bacteria.

SUMMARY OF THE INVENTION

This object is solved by the following method steps:

a) at least one recording of the image of the carrier surface with the collected particles as a color image and digitalization this color image;

b) a conversion of the digitalized color image into a grayscale image or into a grayscale image and, subsequently, into a silhouette image by at least one transformation step, wherein, when particles are present, an image is produced with resulting full-surface labeled objects of a grayscale and a background of a different grayscale;

c) an identification of objects in the grayscale image and/or in the silhouette image by a model-based comparative method;

d) a marking of the contours of identified objects in the color image and/or in the grayscale image;

e) at least one feature determination of the identified objects in the color image and/or in the grayscale image;

f) a case-by-case classification of the objects based on the at least one feature determination;

g) an indication and/or saving of the classified objects as species and/or name and/or code of the classified and thus identified objects; and h) an indication and/or saving of the non-classified objects as a color image and/or grayscale image and/or silhouette image of the thus present, at least one unidentified object, wherein this object subsequently is either discarded or added as a new case with determined class in the classification system.

The method for an automatic identification of microorganisms collected on a carrier that are particles, airborne or present in water, in the form of fungal spores and bacteria is characterized in particular in that certain fungal spores and bacteria are automatically identified as their species and indicated and/or saved. In this way, the method is suitable advantageously for monitoring the atmosphere inside and outside of buildings, wherein the carrier is arranged in the supply air or the atmosphere. However, the method is suitable also for monitoring flowing or standing water, wherein the carrier is moved in the water or placed into flowing water. As a result of the automatic identification of the particles on the carrier surface, which particles are in the form of fungal spores or bacteria, it is possible to react quickly when harmful microorganisms are present as particles in the form of fungal spores and bacteria. In known methods, it is necessary to first cultivate cultures and to manually identify these cultures. This takes several days so that only after a relatively long period of time reliable results are available. A fast reaction is not possible in this way. Advantageously, the particles are automatically identified by the method of the present invention. The special advantage resides in the quick identification of the presence of fungal spores and/or bacteria and the identification of the species of certain fungal spores or bacteria in accordance with the contents of the classification system. For this purpose, the carrier surface with the collected particles is recorded, inclusive of the particles, and the image of the carrier surface is digitalized. This color image, a grayscale image derived therefrom and/or a silhouette image transformed therefrom serves for determining objects within the image. By means of a model-based comparison method, the individual objects are advantageously identified, if present. By means of at least one feature determination, a case-by-case classification of the objects is carried out. The determined objects are advantageously indicated and/or saved as a species. The result is a documentation of the results that are available anytime as the actual result and, subsequently, as a history.

A further important advantage of the method according to the invention resides in that when undetermined and thus non-classified objects are present, they are indicated and/or saved as a color image and/or grayscale image and/or silhouette image. In this way, there is the possibility of identifying these objects manually or to discard them. In the first case, these manually identified objects are added as a new case with a determined class in the classification system. The classification system is thus continuously expanded so that the results of the method can be refined.

In this way, a method for automatic identification of microorganisms collected on a carrier that are particles, airborne or present in water, in the form of fungal spores and bacteria is provided that can be continuously expanded on. This is based on the case-by-case classification system that is upwardly open. Accordingly, the different forms of appearance of the spores or bacteria in their life cycle can also be incorporated into their automatic identification. During their life span, they change their appearance and their size in accordance with the prevailing ambient conditions. Accordingly, different variations of spores and bacteria of each species exist and can be automatically detected by using the method.

Also, the particles deposit in different positions on the carrier surface so that different geometries of each species can be recorded. The method is characterized advantageously also in that these geometries differing with regard to their position can be incorporated into the identification of the spores or bacteria.

Advantageously, in accordance with a further embodiment, in addition to the species the number of identified objects of said species is indicated and/or saved also. In this way, it is possible to also introduce threshold values wherein, for example, an alarm signal is triggered not only when presence is detected but also upon surpassing a certain number of certain particles.

In accordance with another embodiment, advantageously the number of objects that are not identify are counted also so that in the case of a manual identification of these particles immediately their count is also indicated and/or saved. Another repetition based on the expanded classification system is prevented. It is possible to react more quickly to dangerous situations.

In accordance with another embodiment, errors are advantageously purged from the image of the carrier surface with the airborne particles after digitalization and the image is standardized. During standardization, colors and differences of the images are advantageously compensated.

In accordance with another embodiment, further features for the identification of the objects are the shape, the texture, or the structuring of the objects in the color image and/or in the grayscale image. In addition to the outer shape, visually discernable features in the interior of the objects are also incorporated into the identification.

Another embodiment advantageously enables that objects that overlap in the images can be detected with the method according to the invention. Such objects are at least partially overlapping one another. In the case of a large number of particles on the carrier, such arrangements of particles are very likely. For this purpose, the objects that are only partially visually discernable are individualized and compared to objects of the classification system. The objects that are only partially visually discernable are indicated and/or saved. Moreover, the correlated similar objects of the classification system are indicated and/or saved in this connection. At the same time, advantageously the level of congruence is also indicated and/or saved so that by means of a manual comparison the identification can be confirmed or discarded. The number of identified objects rises so that the result of the automatic identification is significantly increased.

In accordance with another embodiment, the image of the carrier surface with the collected particles is recorded as a color image at least once two-dimensionally, sterically and/or three-dimensionally. By means of multiple two-dimensional images of the carrier surface with different depth of field, it is possible advantageously to determine also three-dimensional features of the objects by means of two-dimensional images. The depth of field depends on the adjusted lens width, the focal length, and the aperture. The basis is that when adjusting the lens of the camera to a certain image width, only object points within a certain object width are reproduced in the image plane. The images of object points with smaller object width are produced behind the image plane, and those of the points of greater object width are generated in front of the image plane. A sterical image is created by utilization of holography. In this connection, the hologram can advantageously be recorded by means of different image scales with a camera, for example, in the form of a digital camera. A further advantage resides in that the hologram can be represented with a plane wave at greater or smaller wavelength so that the images are also greater or smaller.

In accordance with another embodiment, advantageously additional objects can be determined by dyeing the carrier surface. Such objects are not recognizable, or only with errors, under normal conditions without dyeing.

In another embodiment, the identification of objects is further improved. A first determination is realized by images of the undyed surface of the carrier. By means of subsequent dyeing, further optical properties of the object can be made visible. A subsequent automatic determination increases the degree of identified objects significantly.

DESCRIPTION OF PREFERRED EMBODIMENTS

A method for automatic identification of microorganisms collected on a carrier that are particles, airborne or present in water, in the form of fungal spores and bacteria will be explained in the following in more detail.

In a first step the carrier surface with the collected particles is recorded as a color image and, advantageously, is simultaneously digitalized. The image is recorded by a device with image enlargement, for example, a microscope with a digital camera, so that for further processing immediately a digitalized image of the carrier surface with the particles is available. This image, in accordance with a first embodiment, is transformed into a grayscale image and, in accordance with a second embodiment, is transformed into a grayscale image and, subsequently, converted into a silhouette image by at least one transformation step. When particles are present, a grayscale image is generated with resulting full-surface labeled objects of one grayscale and a background having a different grayscale. By means of a model-based comparison method, the objects are identified in the grayscale image and/or in the silhouette image. The model in the model-based comparison method is comprised of a quantity of points that describe the contour of the object and the corresponding directional vector. In the past, models such as circles of different size, elliptical shapes of different size and orientation, and rectangles of different size and orientation and having rounded corners have been developed. During the comparison process, the transformed model is compared to the image at any location and a value of similarity between model and image points is generated. The standardized point product of the directional vector of the transformed model and of the vectors is used for generating a comparative value. The standardized level of similarity has the property that it returns a value smaller than one as a result of the comparison. A result of one is produced when model and object are congruent. Moreover, the result corresponds to the proportion of the model that is visible within the image. The model can also be rotated for improving the result so that a result is produced that is greater than the previously determined result and is identical/smaller than one.

The identification of the objects in the grayscale image and/or silhouette image enables marking of the contours of identified objects in the color image and/or in the grayscale image. By means of this marking, the shape, texture, and structure of the identified objects are determined as features in the color image and/or grayscale image. Moreover, based on this, parameters of determined objects can be advantageously calculated also. Such parameters are inter alia surface areas, dimensions in different directions, and the circumference so that additional comparison possibilities are provided. The features form the basis for a subsequent case-by-case classification of the identified objects. The objects that are classified and identified in this way are indicated and/or saved as species, name and/or code.

Determined and non-classified objects are also indicated and/or saved as color images and/or grayscale images and/or silhouette images. Accordingly, these objects can be subsequently either discarded or added as a new case with determined class to the classification system. On the one hand, in this way the saved knowledge in the classification system is expanded and refined, and, on the other hand, the non-classified objects are documented so that later processing can be done also.

In one variant of the embodiment, the objects are additionally counted. This can be done with the classified and identified objects as well as with the non-classified objects. The indication and/or saved values are supplemented by the count, respectively.

For improving the image of the carrier surface with the airborne particles, errors can be purged from the images after recording and digitalization and the images can be standardized by means of image preprocessing.

In a further embodiment, the overlapping particles on the carrier surface are also incorporated into the method for automatic identification of particles collected on a carrier. In this connection, in a first image analysis overlapping particles of the color image or of the grayscale image are separated, removed as objects from the color image, and saved as a partial image. In a second image analysis the overlapping objects of this partial image are separated from another and again saved as a partial image. Features of the objects that can be identified are determined in accordance with the embodiment and, based on these determined features, a comparison with objects in the classification system is carried out. Missing areas can be supplemented in that a determination of these objects is also provided. Advantageously, the original and individualized object, the identified object that has been determined by the supplement, and the level of congruence and thus of the magnitude of the supplement for a manual identification is indicated and/or saved for documentation purposes.

In another embodiment, the carrier surface can be dyed for improving the identification of the particles. The dyeing action can be done prior to recording as well as after recording an image.

What is claimed is:

1. A method for automatic identification of microorganisms collected on a carrier, which microorganisms are fungal spores and bacteria and are airborne or present in water, the method comprising the steps of:
   a) recording at least one color image of a carrier surface with collected microorganisms with a digital device with image enlargement that digitalizes the at least one color image to a digitalized color image so that for further processing immediately a digitalized image of the carrier surface with the microorganisms is available;
   b) converting the digitalized color image into a grayscale image and optionally converting subsequently the grayscale image into a silhouette image and producing, when microorganisms are present on the carrier, an image with resulting full-surface labeled objects, representing the microorganisms, of a first grayscale and a background of a different second grayscale;
   c) comparing the objects to models by a model-based comparative method in order to identify identified objects and unidentified objects in at least one of the grayscale image and the silhouette image;
   d) marking contours of the identified objects in the at least one of the color image and the grayscale image;
   e) determining at least one feature of the identified objects in the at least one of the color image and the grayscale image;
   f) classifying case-by-case the identified objects based on the at least one feature as classified objects with a classification system;
   g) counting all the objects to determine a count of the identified objects and of the non-classified unidentified objects;
   h) indicating; saving; or indicating and saving the classified objects as at least one of species; name; and code together with the count of the classified objects;
   i) indicating; saving; or indicating and saving the non-classified, unidentified objects as at least one of a color image; grayscale image; and silhouette image together with the count and subsequently discarding the non-classified, unidentified objects or adding the non-classified, unidentified objects as a new case with determined class in the classification system;
   j) separating overlapping objects in the color image or in the grayscale image by performing a first image analysis and removing the overlapping objects from the color image or the grayscale image and saving the overlapping objects as a first partial image;
   k) separating by a second image analysis the overlapping objects of the first partial image from one another and saving the separated overlapping objects as second partial images;
   l) determining features of the separated overlapping objects and, by comparison with saved and identified objects of the classification system, identifying supplemented objects and supplementing missing areas caused by overlap;
   m) indicating; saving; or indicating and saving the identified separated objects of the step k), the supplemented objects of the step l), and a level of congruence between the supplemented objects of step l) and the correlated saved and identified objects of the classification system.

2. The method according to claim 1, further comprising the step of purging, after the step of recording, errors from the color image of the carrier surface and standardizing the color image subsequently by image preprocessing.

3. The method according to claim 1, wherein the at least one feature is a shape, a texture or a structure of the identified objects in the at least one of the color image and the grayscale image.

4. The method according to claim 1, wherein the step of recording comprises recording the color image of the carrier surface at least once two-dimensionally or sterically or three-dimensionally.

5. The method according to claim 1, further comprising the step of dyeing the carrier surface prior to recording the color image of the carrier surface.

6. The method according to claim 1, further comprising the steps of:
   dyeing the carrier surface after the step of recording the at least one color image of the carrier surface;
   recording at least one additional color image of the dyed carrier surface; and
   digitalizing the at least one additional color image and performing the steps b) to i) for the at least one color image of the carrier surface recorded before the step of dyeing and for the at least one additional image of the dyed carrier surface.

7. The method according to claim 1, comprising the step of triggering an alarm when a threshold value for the count of identified objects is surpassed or a certain species is identified.

8. The method according to claim 1, comprising the step of documenting the results of the steps h), i) and m).

* * * * *